(12) United States Patent
Egboiyi et al.

(10) Patent No.: US 10,962,457 B2
(45) Date of Patent: Mar. 30, 2021

(54) APPARATUS AND METHODS TO IMPACT TEST MATERIALS (71) Applicant: CORNING INCORPORATED, Corning, NY (US)

(72) Inventors: Benedict Osobomen Egboiyi, Painted Post, NY (US); Kevin Barry Reiman, Horseheads, NY (US); Brian Paul Strines, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 308 days.

(21) Appl. No.: 15/771,656

(22) PCT Filed: Oct. 28, 2016

(86) PCT No.: PCT/US2016/059243
§ 371 (c)(1),
(2) Date: Apr. 27, 2018

(87) PCT Pub. No.: WO2017/075301
PCT Pub. Date: May 4, 2017

(65) Prior Publication Data
US 2018/0313728 A1 Nov. 1, 2018

Related U.S. Application Data

(60) Provisional application No. 62/248,475, filed on Oct. 30, 2015.

(51) Int. Cl.
*G01N 3/303* (2006.01)
*G01N 3/04* (2006.01)
(Continued)

(52) U.S. Cl.
CPC ............. *G01N 3/303* (2013.01); *G01N 3/04* (2013.01); *G01N 3/30* (2013.01); *G01N 33/386* (2013.01);
(Continued)

(58) Field of Classification Search
None
See application file for complete search history.

(56) References Cited

U.S. PATENT DOCUMENTS 3,877,969 A * 4/1975 Tatsumi ............. C03C 17/3405
215/12.2
6,305,492 B1 * 10/2001 Oleiko .................. E01F 8/0017
181/210
(Continued)

FOREIGN PATENT DOCUMENTS

CN 202956317 U 5/2013
CN 203643120 U 6/2014
(Continued)

OTHER PUBLICATIONS

English Translation of CN201680064065.X Office Action dated Apr. 3, 2020; 16 Pages; Chinese Patent Office.
(Continued)

*Primary Examiner* — Jill E Culler
(74) *Attorney, Agent, or Firm* — Kevin M. Johnson (57) ABSTRACT

Apparatus and methods for impact testing of a transparent substrate are provided. The apparatus includes a base (110) for receiving the transparent substrate (112), the base having a curved surface (124) about which the transparent substrate is bent by a first fixture (130) and a second fixture (132). An abrasive sheet (136) is disposed between the transparent substrate and an impacting object (138) which is released from above the substrate such that the force from the impacting object causes damage to the transparent substrate
(Continued)

while the transparent substrate is bent about the curved surface.

25 Claims, 4 Drawing Sheets

(51) Int. Cl.
 *G01N 33/38* (2006.01)
 *G01N 3/30* (2006.01)
(52) U.S. Cl.
 CPC ........ *G01N 2203/0246* (2013.01); *G01N 2203/0282* (2013.01)

(56) References Cited

U.S. PATENT DOCUMENTS

| | | | |
|---|---|---|---|
| 7,516,644 B2 | 4/2009 | Wong et al. | |
| 9,552,747 B1* | 1/2017 | Lytle | G09B 23/30 |
| 2009/0087647 A1* | 4/2009 | Nakagawa | G02F 1/1333 |
| | | | 428/336 |
| 2011/0072856 A1 | 3/2011 | Davidson et al. | |
| 2014/0150525 A1 | 6/2014 | Okawa et al. | |
| 2014/0370264 A1* | 12/2014 | Ohara | G06F 1/1626 |
| | | | 428/220 |
| 2015/0239775 A1* | 8/2015 | Amin | C03C 3/091 |
| | | | 428/220 |
| 2015/0259244 A1 | 9/2015 | Amin et al. | |
| 2017/0022092 A1* | 1/2017 | DeMartino | C03C 21/002 |
| 2020/0109079 A1* | 4/2020 | Da | C03C 3/085 |

FOREIGN PATENT DOCUMENTS

| | | |
|---|---|---|
| CN | 204389140 U | 6/2015 |
| CN | 105022919 A | 11/2015 |
| JP | 2002372485 A | 12/2002 |
| JP | 2009276140 A | 11/2009 |

OTHER PUBLICATIONS

Ohkawa et al; "Product Design for Strong Cover Glass"; Journal of the SID; 23/3, 2015; pp. 119-128.

International Search Report and Written Opinion of the International Searching Authority; PCT/US2016/059243; dated Jan. 17, 2017; 14 Pages; European Patent Office.

Nakagawa et al; "Establishment of Evaluation Method of Surface Fracture Mode With Front-Side-Origin for Cover Glass"; Online Library, wiley.com; 4 Pages; http://onlinelibrary.wiley.com/doi/10.1002/j.2168-0159.2013.tb06430.x/pdf.

* cited by examiner

APPARATUS AND METHODS TO IMPACT TEST MATERIALS

CROSS-REFERENCE TO RELATED APPLICATIONS

This application is a national stage entry of International Patent Application Serial No. PCT/US16/059243 filed on Oct. 28, 2016, which claims the benefit of priority under 35 U.S.C. § 119 of U.S. Provisional Application Ser. No. 62/248,475 filed on Oct. 30, 2015 the content of which is relied upon and incorporated herein by reference in its entirety.

FIELD

Embodiments of the disclosure generally relate to apparatus and methods for impact testing materials. More particularly, embodiments of the disclosure are directed to apparatus and methods for simulating damage to the cover glass of a handheld electronic device.

BACKGROUND

Handheld electronic devices such as mobile phones and tablets include a cover substrate, which is typically a glass substrate, which is typically referred to as a cover glass. Understanding the failure mechanism of a cover glass when the handheld device is dropped is important to determine ways to prevent cover glass failure and improving materials used to manufacture cover glass. This understanding is especially important with the movement towards thinner and lighter cover glass materials. Variations in material properties such as ion exchange variations can be better understood if the failure mechanism is more accurately reproduced compared with existing methods.

One way to drop test cover substrate materials is to retrofit a cover substrate into commercially available phones. While the test results are useful and are able to adequately differentiate between different materials, the phones are expensive and the process of retrofitting is time intensive. "Pucks" that represent the size, shape and mass of typical cell phones are also used. While less costly than phones, fitting materials into the pucks is still a time intensive process.

The retrofit process and drop testing work well in that the failure of the cover material replicates the failure mode typically seen in the field: sharp-contact damage to the cover while the cover is convexly bent. Existing test methods have provided a limited understanding of the failure mechanism when a handheld device is dropped, which will be referred to as "a drop event." Therefore, there is a need for apparatus and methods for impact testing of substrate materials that more accurately reproduce the stresses experienced by the cover glass of a handheld device during a drop event.

SUMMARY OF THE CLAIMS

One or more embodiments of the disclosure are directed t an apparatus for impact testing a transparent substrate, the apparatus including a base for receiving a transparent substrate having at least two ends, an inner surface and an outer surface, the base having a first end and a second end, and a curved surface defining a radius of curvature between the first end and the second end; a first fixture and a second fixture to hold the at least two ends of the transparent substrate and to apply a force to bend the transparent substrate about the curved surface and to conform the transparent substrate to the radius of curvature; an abrasive sheet having an abrasive surface to be placed in contact with the outer surface of the transparent substrate; and an impacting object positioned above the base, the impacting object to be released from above the base such that the force from impacting object causes damage to the transparent substrate while the transparent substrate is bent about the curved surface.

Another aspect of the disclosure pertains to a method of impact testing a transparent substrate including placing a transparent substrate on the curved surface of the apparatus described herein; bending the transparent substrate about the curved surface; securing the at least two ends of the transparent substrate with the first fixture and second fixture to provide an apex on the outer surface of the transparent substrate; and releasing the impacting object positioned above the base while the transparent substrate is bent about the curved surface.

In one or more embodiments, a method of impact testing a transparent sheet includes bending the transparent sheet having an impacting surface to a radius of curvature to create an apex on the impacting surface; and impacting the transparent sheet at the apex with an impacting object. In variants on this embodiment, the transparent sheet is glass and the radius of curvature is in a range that simulates a bending radius of a chemically or thermally strengthened cover glass of a mobile phone or tablet device when the mobile phone or tablet device is dropped on a ground surface by a user of the mobile phone or tablet device. In another variant, an abrasive sheet is placed in contact with the impacting surface of the transparent sheet and a plate is placed on the abrasive sheet prior to impacting the transparent sheet at the apex. In another variant, the transparent sheet is secured to a curved surface prior to impacting the apex with the impacting object. In some embodiments, the impacting object is a ball comprising one or more of metal and ceramic materials, and the plate comprises a material comprising one or more of metal and ceramic materials. In specific embodiments, the impacting object is released from a vacuum chuck.

BRIEF DESCRIPTION OF THE DRAWINGS

The accompanying figures, which are incorporated in and constitute a part of this specification, illustrate several embodiments described below.

DETAILED DESCRIPTION

Embodiments of the disclosure provide apparatus and methods for impact testing substrates, in particular, transparent substrates, for example sheets of glass. In one or more embodiments, the apparatus and methods simulate the bending radius of a strengthened cover glass of a handheld device when the handheld electronic device is dropped on a ground surface by a user of the handheld electronic device. According to one or more embodiments, the methods and apparatus described herein provide the ability to differentiate between different materials, the same materials of different thicknesses and the same materials of the same thickness with different ion exchange treatments, in the case of ion exchanged-chemically strengthened glass material.

The apparatus and methods described herein can be used to impact test substrates that are typically used as cover substrates for handheld electronic devices. Such handheld electronic devices according to one or more embodiments typically have a display screen. Non-limiting examples of handheld electronic devices include a mobile telephone, a reading device, a music device, a viewing device and a navigation device. Non-limiting examples of such devices are iPhone®, Nook®, iPod®, iPad®, Droid®, Kindle® and GPS navigation systems.

According to one or more embodiments, the apparatus and methods are used for testing substrates used to cover the displays of handheld electronic devices. Such substrates are transparent substrates or transparent sheets in one or more embodiments. The substrates can be amorphous substrates or crystalline substrates. Amorphous substrates according to one or more embodiments can be selected from soda lime glass, alkali aluminosilicate glass, alkali containing borosilicate glass and alkali aluminoborosilicate glass. In one or more embodiments, the substrate is a glass, and the glass can be strengthened, for example, heat strengthened, tempered glass, or chemically strengthened glass. In one or more embodiments, strengthened glass substrates have a compressive stress (CS) layer with a CS extending within the chemically strengthened glass from a surface of the chemically strengthened glass to a compressive stress depth of layer (DOL) of at least 5 μm to several tens of microns deep. In one or more embodiments, the glass substrate is a chemically strengthened glass substrate such as Corning Gorilla® glass. Examples of crystalline materials include glass-ceramic substrates such as sapphire and spinel ($MgAl_2O_4$).

FIGS. 1 through 4 show a measurement apparatus 100 for impact testing a substrate as provided above in accordance with one or more embodiments of the disclosure. The apparatus 100 includes a base 110 for receiving a transparent substrate 112 having at least two ends 114, 116, an inner surface 113 and an outer surface 115. The base 110 has a first end 120 and a second end 122, and a curved surface 124 defining a radius of curvature between the first end 120 and the second end 122. The base 110 can be any suitable material to provide a platform to secure a substrate for the impact test, which will be described further below. Suitable materials for the base 110 can include wood, metal ceramic or combinations thereof. The curved surface 124 has an apex 125.

The measurement apparatus 100 according to one or more embodiments further includes a first fixture 130 and a second fixture 132 to hold the at least two ends 114, 116 of the transparent substrate and to apply a force to bend the transparent substrate 112 about the curved surface 124 and to conform the transparent substrate to the radius of curvature. By bending the transparent substrate 112, the glass substrate has an apex 127 conforming to the apex 125 of the curved surface 124. In one or more specific embodiments, the curved surface 124 and the curvature of the transparent substrate 112 can be a fixed radius or a compound radius.

The measurement apparatus 100 according to one or more embodiments further includes an abrasive sheet 136 having an abrasive surface to be placed in contact with the outer surface of the transparent substrate. The measurement apparatus 100 according to one or more embodiments further includes an impacting object 138 positioned above the base 110, the impacting object 138 to be released from above the base 110 such that the force from impacting object 138 causes damage to the transparent substrate 112 while the substrate is bent about the curved surface 124.

In one or more embodiments, the measurement apparatus 100 further includes a plate 140 to be positioned on the abrasive sheet 136 such that the plate 140 is contacted by the impacting object 138. According to one or more embodiments, the transparent substrate 112 is glass and the radius of curvature is in a range that simulates a bending radius of a chemically strengthened cover glass of a mobile phone or tablet device when the mobile phone or tablet device is dropped on a ground surface by a user of the mobile phone or tablet device. In specific embodiments, the radius of curvature is in the range of 0.25 meters (m) and 1.5 meters; or 0.25 meters and 1.3 meters; 0.25 meters and 1.2 meters; or 0.25 meters and 1 meter; or 0.5 meters and 1.5 meters, 0.25 meters and 1.3 meters and 0.5 meters and 1.2 meters; or 0.5 and 1 meter.

Figure 1:
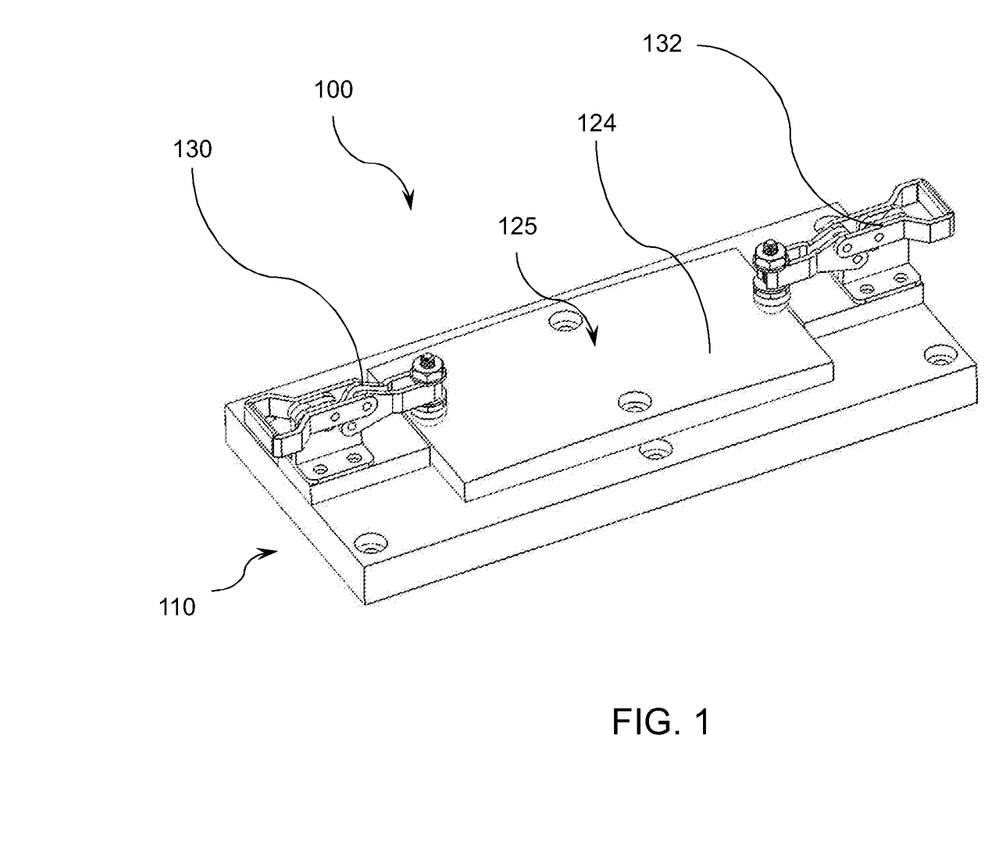
FIG. 1 shows perspective view of an apparatus to impact test a substrate in accordance with one or more embodiments of the disclosure.
Figure 2:
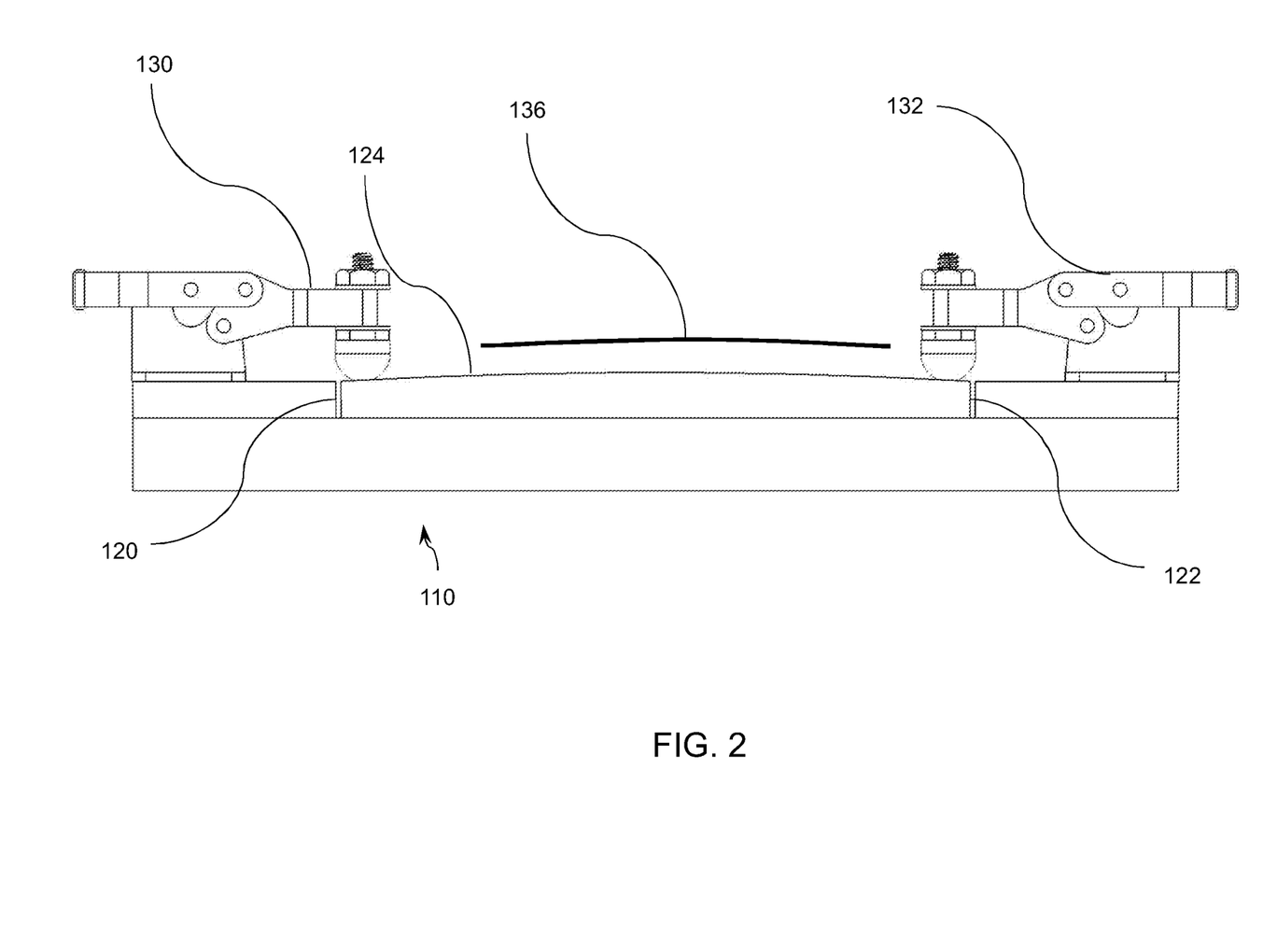
FIG. 2 shows a side view of the apparatus in FIG. 1.
Figure 3:
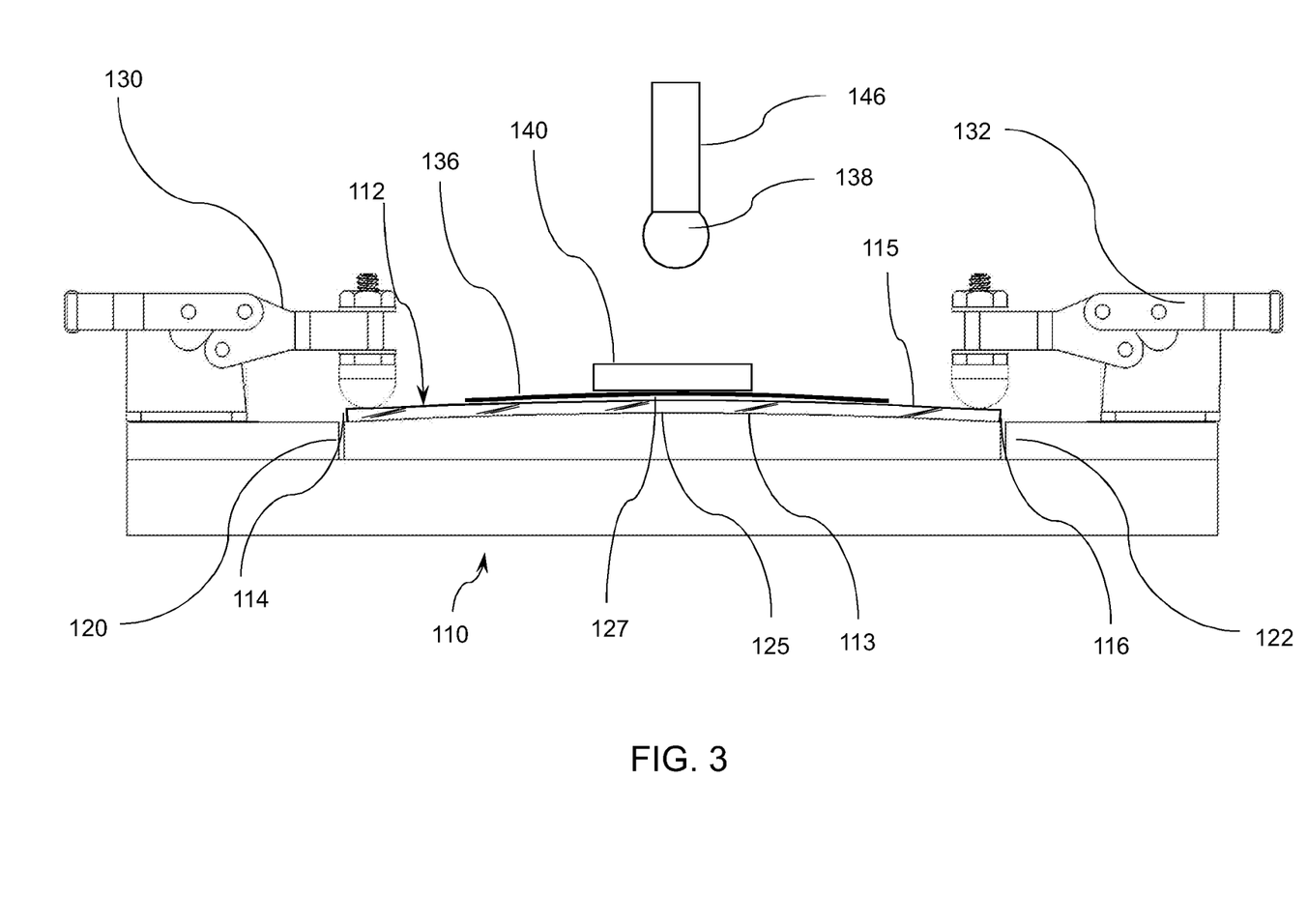
FIG. 3 shows the apparatus in FIG. 2, including an impacting object.
Figure 4:
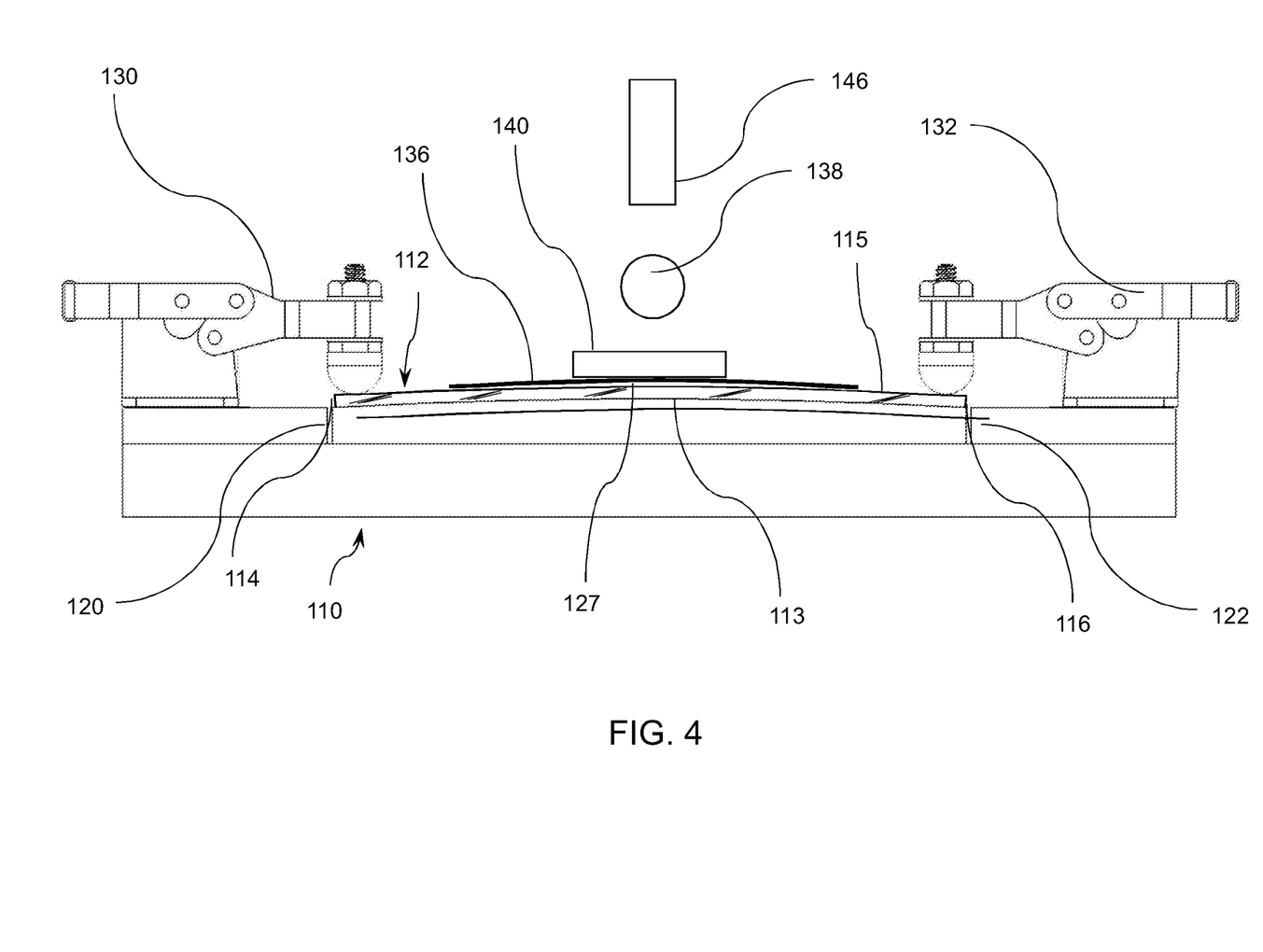
FIG. 4 shows the apparatus in FIG. 3 with the impacting object released and falling towards the substrate.

The impacting object 138 is retained in place by retaining fixture 146, which releasably holds the impacting object above the base 110 until it is ready to be released. The retaining fixture 146 can be any suitable structure to hold and release the impacting object 138. In one or more embodiments, the retaining fixture 146 comprises a shelf, a claw, or tongs. In specific embodiments, the retaining fixture 146 comprises a vacuum chuck with a vacuum line (not shown) attached to the retaining fixture. When the impacting object 138 is held above the base 110, vacuum is applied so that the retaining fixture 146 exerts a force sufficient to prevent the object from falling. When the impacting object 138 is released, the vacuum is released, allowing the impacting object 138 to fall and hit the plate 140. The impacting object 138 and the retaining fixture 146 are positioned above the base at a distance in the range of 5 cm and 500 cm. In one or more embodiments, the impacting object hits the plate 140 within 2 mm or 1 mm of the apex 127. When the impacting object 138 is dropped, the base of the apparatus 100 should be flat and horizontal.

In most handheld device field failures (i.e., failure of devices in real world conditions) where cover glass failure originates on the surface, failure is a result of damage introduction while a tensile force is applied to the cover glass surface via bending. It was determined that while dropping the impacting object 138 on the transparent substrate 112 bent about the curved surface provided a more realistic reproduction of forces during a drop event, failure analysis of substrates tested without a plate 140 between the transparent substrate 112 and impacting object 138 revealed a pitting of the transparent substrate surface caused by repeated drops on the same spot. When testing thermally or chemically strengthened glass substrate with a compressive stress (CS) layer depth of layer (DOL), pitting can penetrate the DOL, which can cause failure inconsistent with observed field failures modes. A second problem associated with dropping the impacting object 138 directly on the transparent substrate 112 is that that localized stresses caused by the impacting object 138 caused ring failures, which are not observed in typical field failures.

Utilization of the plate 140 placed between the impacting object 138 and the transparent substrate 112 addressed one or more of the above issues. It was determined that the plate 140 distributes the forces across a larger area of the transparent substrate 112, accomplished by centering the plate 140, on top of the abrasive sheet 136. According to one or more embodiments, the force of the impacting object 138 drop transmits through the plate 140 and into the abrasive sheet 136, nominally into the short-axis centerline of the transparent substrate 112 (i.e. the line forming the apex of a specimen clamped to the curved surface 124). In a specific embodiment, it was determined that since the force from the impacting object drop was distributed across a larger area, a larger impacting object (16.3 g instead of 4.1 g) was used to produce the desired range of failure heights. It was determined that with the plate 140 in place, ring failures were eliminated resulting in failures typical of those observed in the field (damage introduction during bending) for all specimens tested.

In specific embodiments, the first fixture 130 and second fixture 132 are spaced apart at a distance of a cover glass length for a mobile phone or a tablet, for example in a range of about 50 mm and 500 mm. A very specific embodiment provides an apparatus suitable to test a substrate that is 110 mm×57 mm. According to one or more embodiments, the first fixture 130 and the second fixture 132 each are a clamp, and in specific embodiments toggle clamps as shown in the Figures. In other specific embodiments, the abrasive sheet comprises sandpaper, which may have a grit size in the range of 30 grit to 400 grit, or 100 grit to 300 grit, for example 180 grit. One suitable sandpaper is Indasa Rhynowet® Plus Line P180 grit sandpaper. The sandpaper according to one or more embodiments is cut in 25 mm square pieces, and the sandpaper is flattened if the pieces are bent during the cutting process. In other specific embodiments, clamping bars (not shown) may be provided and positioned between the first fixture 130 and the transparent substrate 112 and the second fixture 132 and the transparent substrate 112. The clamping bars can be rectangular bars to distribute the clamping force across the transparent substrate 112. In other specific embodiments, it may be desirable to include a buffer layer (not shown) on the inner surface 113 of the transparent substrate 112. A suitable buffer layer can be tape such as masking tape, vinyl tape or electrical tape. There should be no trapped air present after taping the inner surface 113.

The impacting object 138 according to one or more embodiments can be any suitable shape, but in specific embodiments, the impacting object 138 is spherical in shape, e.g., a ball. The plate 140 according to one or more embodiments is generally rectangular in shape, however, other shapes are possible such as circular or disc-shaped. In one or more embodiments, the impacting object 138 and the plate 140 are made from a material selected from one or more of metal or polymer or composite materials. Composite materials can include metal-ceramic composites, metal-polymer composite or polymer-ceramic materials. In specific embodiments, the impacting object 138 is made from a material that has a hardness that is greater than the hardness of the plate 140. In a highly specific embodiment, the impacting object 138 can be a chrome steel alloy E52100 ball having a diameter in the range of about 10 mm and 16 mm. It will be understood that the diameter of the impacting object 138 will be chosen depending on the density of the material used to make the impacting object. Thus, lower density materials may utilize a larger diameter impacting object 1138. The diameter of the impacting object may be in the range of 5 mm and 40 mm, and more specifically in the range of 5 mm and 25 mm.

In specific embodiments, the impacting object 138 is positioned so that the impacting object cause the plate 140 and abrasive sheet 136 to contact the transparent substrate apex.

Another aspect of the disclosure pertains to a method of impact testing a transparent substrate 112. The method according to one or more embodiments includes placing a transparent substrate 112 on the curved surface 124 of the apparatus 100 described above, bending the transparent substrate about the curved surface 124, and securing the at least two ends of the transparent the substrate with the first fixture and second fixture to provide the apex 127 on the outer surface of the transparent substrate 112. The method further includes releasing the impacting object 138 positioned above the base while the transparent substrate 112 is bent about the curved surface 124.

In one or more embodiments of the method, the impacting object 138 is a ball, and the method further includes disposing the plate 140 between the transparent substrate and the abrasive sheet. In specific embodiments, the impacting object 138, which hits the plate 140 causes sharp contact damage to the transparent substrate 112. In other specific method embodiments, the transparent substrate 112 is glass and securing the at least two ends of the transparent substrate 112 comprises clamping the at least two ends of the transparent substrate 112. In other specific embodiments, the impacting object 138 can be released from a vacuum chuck as described above. According to one or more embodiments, the plate 140 can be held in place with a suitable holding mechanism. In one embodiment, the holding mechanism can be a yoke (not shown) configured to maintain the plate 140 in a horizontal orientation, yet allow the plate 140 to conform to the substrate/abrasive stack. The holding mechanism can prevent wobbling of the plate 140 when the impacting object is off center, thus helping to center the damage on the specimen apex. In specific embodiments, the yoke is thinner than the plate 140 to limit contact during the drop event to only the plate 140. The height of the yoke and plate relative to the fixture would be adjustable to keep the central horizontal planes of the yoke and the plate parallel. In specific embodiments, the yoke could be held in place with a hinge to allow freedom of movement and full contact of the plate to the abrasive.

Other method embodiments pertain to a method of impact testing a transparent sheet, including bending the transparent sheet having an impacting surface to a radius of curvature to create an apex on the impacting surface and impacting the transparent sheet at the apex with an impacting object. In specific embodiments, the transparent sheet is glass and the radius of curvature is in a range that simulates a bending radius of a chemically or thermally strengthened cover glass of a mobile phone or tablet device when the mobile phone or tablet device is dropped on a ground surface by a user of the mobile phone or tablet device. In specific embodiments, the glass sheet is Gorilla® glass available from Corning, Incorporated. In other specific embodiments, an abrasive sheet is placed in contact with the impacting surface of the transparent sheet and a plate is placed on the abrasive sheet prior to impacting the transparent sheet at the apex. In one or more embodiments, the transparent sheet is secured to a curved surface prior to impacting the apex with the impacting object.

According to one or more embodiments, a specific test method includes providing a curved support surface and securely attaching the curved support surface to a base. A substrate or sheet (test specimen) is clamped on the curved surface of the fixture as described above, and a sandpaper sheet is centered on top of the substrate or sheet. A metal plate is centered on top of the sandpaper. Then an impacting object in the form of a metal ball is dropped from a height of 10 cm. If the test specimen does not fail, increase the ball drop height by 10 cm, and perform a second ball drop. If the test specimen fails, record the failure height and proceed to the next test specimen and a new sheet of sandpaper. If the test specimen does not fail, proceed to the next drop height increment using the same piece of sandpaper. The testing continues in this manner until the test specimen fails or the maximum drop height is reached.

If the sandpaper sheet has an insufficient amount of unused area remaining, a new sandpaper sheet should be used—for a test where the initial drop height is 5 cm and the height increment is 5 cm, this occurs at the 100 cm drop height. If the maximum drop height is reached, record the failure or non-failure of the test specimen. Variations to the method and apparatus can include adjusting the failure height range by using sandpapers of different grit to alter the level of damage introduction. The sandpaper dimensions may be altered to change the force per unit area applied to the test specimen. The ball composition/density/mass may be altered to adjust the force applied to the top plate. The support compliance can be changed by changing the specimen tape or the curved support material. In addition, the starting drop height and drop height increment may be adjusted. Furthermore, alternate plate dimensions or materials may be used, but the during a drop, the plate should sustain damage, not the impacting object (ball).

Provided herein is an apparatus and method that can be used to accurately simulate the bending radius of a chemically or thermally strengthened cover glass of a mobile phone or tablet device when the mobile phone or tablet device is dropped on a ground surface by a user of the mobile phone or tablet device. By simulating the bending radius and dropping the impacting object with the plate and abrasive sheet disposed between the impacting object and the sheet that is tested, a more accurate simulation of the forces and impact experienced by a cover glass of a handheld electronic device is provided. In one or more embodiments, the methods and apparatus described herein are particularly useful for impact testing glass substrate that are used in mobile phones and tablets, and in particular, glass that has tension on the outside surface of the glass substrate and compression on the inside surface of the glass substrate. A specific example of such a glass substrate is Gorilla® glass.

While the foregoing is directed to various embodiments, other and further embodiments of the disclosure may be devised without departing from the basic scope thereof, and the scope thereof is determined by the claims that follow.

What is claimed is:

1. An apparatus for impact testing a transparent substrate comprising:
    a base for receiving a transparent substrate having at least two ends, an inner surface and an outer surface, the base having a first end and a second end, and a curved surface defining a radius of curvature that is not zero between the first end and the second end;
    a first fixture and a second fixture to hold the at least two ends of the transparent substrate and to apply a force to bend the transparent substrate about the curved surface and to conform the transparent substrate to the radius of curvature;
    an abrasive sheet having an abrasive surface to be placed in contact with the outer surface of the transparent substrate; and
    an impacting object positioned above the base, the impacting object to be released from above the base such that the force from impacting object causes damage to the transparent substrate while the transparent substrate is bent about the curved surface.

2. The apparatus of claim 1, further comprising a plate to be positioned on the abrasive sheet such that the plate is contacted by the impacting object.

3. The apparatus of claim 2, wherein the transparent substrate is glass and the radius of curvature is in a range that simulates a bending radius of a chemically strengthened cover glass of a mobile phone or tablet device when the mobile phone or tablet device is dropped on a ground surface by a user of the mobile phone or tablet device.

4. The apparatus of claim 3, the radius of curvature is in the range of 0.25 m and 1.5 m.

5. The apparatus of claim 3, wherein the radius of curvature is in the range of 0.5 m and 1 m.

6. The apparatus of claim 5, wherein the first fixture comprises a first clamp and the second fixture comprises a second clamp.

7. The apparatus of claim 6, wherein the first clamp and the second clamp comprise toggle clamps.

8. The apparatus of claim 2, wherein the first fixture and second fixture are spaced apart at a distance of a cover glass length for a mobile phone or a tablet.

9. The apparatus of claim 8, wherein the first fixture and second fixture are spaced apart at a distance in the range of 50 mm and 500 mm.

10. The apparatus of claim 2, wherein the abrasive sheet comprises sandpaper.

11. The apparatus of claim 10, wherein the sandpaper has a grit size of 180.

12. The apparatus of claim 2, wherein the impacting object comprises a ball made from a material selected from one or more of metal or polymer or composite materials and the plate comprises a material selected from one or more of metal and polymer and composite materials.

13. The apparatus of claim 2, where the impacting object comprises a chrome steel alloy ball having a diameter in the range of 10 mm and 16 mm and the apparatus further comprises a vacuum chuck positioned above the base to releasably hold the ball above the base.

14. The apparatus of claim 2, wherein the impacting object is positioned above the curved surface at a distance in the range of 5 cm and 500 cm.

15. The apparatus of claim 2, wherein the curved surface has an apex, and the transparent substrate bent about the curved surface has a transparent substrate apex, and the impacting object is positioned so that the impacting object cause the plate and the abrasive sheet to contact the transparent substrate apex.

16. A method of impact testing a transparent substrate comprising:
    placing a transparent substrate on the curved surface of the apparatus of claim 1;
    bending the transparent substrate about the curved surface;
    securing the at least two ends of the transparent substrate with the first fixture and second fixture to provide an apex on the outer surface of the transparent substrate; and
    releasing the impacting object positioned above the base while the transparent substrate is bent about the curved surface.

17. The method of claim 16, wherein the impacting object is a ball, and the method further comprises disposing a plate comprising a material including one or more of metal and ceramic materials between the transparent substrate and the abrasive sheet.

18. The method of claim 17, wherein the transparent substrate is glass and securing the at least two ends of the transparent substrate comprises clamping the at least two ends of the transparent substrate.

19. The method of claim 18, wherein the ball is released from a vacuum chuck.

20. A method of impact testing a transparent sheet, the method comprising:
bending the transparent sheet having an impacting surface about a curved surface of a base, the base having a first end and a second end, and the curved surface defining a radius of curvature that is not zero between the first end and the second end to create an apex on the impacting surface; and
impacting the transparent sheet at the apex with an impacting object, wherein an abrasive sheet is placed in contact with the impacting surface of the transparent sheet.

21. The method of claim 20, wherein the transparent sheet is glass and the radius of curvature is in a range that simulates a bending radius of a chemically or thermally strengthened cover glass of a mobile phone or tablet device when the mobile phone or tablet device is dropped on a ground surface by a user of the mobile phone or tablet device.

22. The method of claim 20, wherein an abrasive sheet is a plate is placed on the abrasive sheet prior to impacting the transparent sheet at the apex.

23. The method of claim 22, wherein the transparent sheet is secured to a curved surface prior to impacting the apex with the impacting object.

24. The method of claim 23, wherein the impacting object is a ball comprising one or more of metal and ceramic materials and the plate comprises a material comprising one or more of metal and ceramic materials.

25. The method of claim 24, wherein the ball is released from a vacuum chuck.

\* \* \* \* \*

UNITED STATES PATENT AND TRADEMARK OFFICE
CERTIFICATE OF CORRECTION

PATENT NO. : 10,962,457 B2
APPLICATION NO. : 15/771656
DATED : March 30, 2021
INVENTOR(S) : Benedict Osobomen Egboiyi et al.

Page 1 of 1

It is certified that error appears in the above-identified patent and that said Letters Patent is hereby corrected as shown below:

In the Claims

In Column 10, Line 5, Claim 22, after "wherein" delete "an abrasive sheet is".

Signed and Sealed this
First Day of June, 2021

Drew Hirshfeld
*Performing the Functions and Duties of the*
*Under Secretary of Commerce for Intellectual Property and*
*Director of the United States Patent and Trademark Office*